(12) United States Patent
Bunshaw et al.

(10) Patent No.: US 12,273,448 B2
(45) Date of Patent: Apr. 8, 2025

(54) SECURE INFORMATION SHARING SYSTEMS AND METHODS

(71) Applicant: DB RESULTS PTY LTD, Melbourne (AU)

(72) Inventors: Gavin Bunshaw, Melbourne (AU); Leon Madafferi, Melbourne (AU); Rallas Buttriss, Melbourne (AU)

(73) Assignee: DB RESULTS PTY LTD, Melbourne (AU)

( * ) Notice: Subject to any disclaimer, the term of this patent is extended or adjusted under 35 U.S.C. 154(b) by 490 days.

(21) Appl. No.: 17/633,779

(22) PCT Filed: Aug. 13, 2020

(86) PCT No.: PCT/AU2020/050844
§ 371 (c)(1),
(2) Date: Feb. 8, 2022

(87) PCT Pub. No.: WO2021/026611
PCT Pub. Date: Feb. 18, 2021

(65) Prior Publication Data
US 2022/0278830 A1    Sep. 1, 2022

(30) Foreign Application Priority Data

Aug. 13, 2019 (AU) ................................ 2019902918

(51) Int. Cl.
*H04L 9/08* (2006.01)
*G06Q 20/38* (2012.01)
*H04L 9/40* (2022.01)

(52) U.S. Cl.
CPC ......... *H04L 9/088* (2013.01); *G06Q 20/3829* (2013.01); *H04L 63/0428* (2013.01); *G06Q 2220/00* (2013.01)

(58) Field of Classification Search
CPC . H04L 9/088; H04L 63/0428; G06Q 20/3829; G06Q 2220/00
See application file for complete search history.

(56) References Cited

U.S. PATENT DOCUMENTS 10,484,354 B2 * 11/2019 Casella ................. H04L 63/061
10,797,861 B2 * 10/2020 Li ........................... H04L 63/12
(Continued)

FOREIGN PATENT DOCUMENTS

WO    2019/078879    4/2019

OTHER PUBLICATIONS

Dagher, et al., "Ancile: Privacy-Preserving Framework for Access Control and Interoperability of Electronic Health Records Using Blockchain Technology", Sustainable Cities and Society, vol. 39, pp. 283-297, Feb. 17, 2018.
(Continued)

*Primary Examiner* — Kambiz Zand
*Assistant Examiner* — Afaq Ali
(74) *Attorney, Agent, or Firm* — Barnes & Thornburg LLP (57) ABSTRACT

Some embodiments relate to systems and method for secure information sharing using an information sharing engine. The information sharing engine configured to manage data access keys and data access control configuration, store the data access keys and data access control configuration on a distributed ledger network and selectively retrieve the data access keys from the distributed ledger network based on the data access control configuration.

16 Claims, 8 Drawing Sheets

(56) References Cited

U.S. PATENT DOCUMENTS

| | | | |
|---|---|---|---|
| 11,146,541 B2* | 10/2021 | Roth | H04L 63/06 |
| 11,582,040 B2* | 2/2023 | Soundararajan | H04L 63/10 |
| 2009/0037743 A1* | 2/2009 | Narayanaswami | G07C 9/37 |
| | | | 713/186 |
| 2016/0055347 A1* | 2/2016 | Park | G06F 21/602 |
| | | | 713/165 |
| 2017/0300627 A1 | 10/2017 | Giordano et al. | |
| 2019/0294817 A1* | 9/2019 | Hennebert | H04L 9/0861 |
| 2020/0372168 A1* | 11/2020 | Stow | G06F 21/602 |
| 2022/0060514 A1* | 2/2022 | Hu | H04L 9/3213 |

OTHER PUBLICATIONS

Liang, X. et al., "Integrating Blockchain for Data Sharing and Collaboration in Mobile Healthcare Applications" International Symposium on Personal, Indoor, and Mobile Radio Communications (PIMRC), Oct. 8, 2017.

Mounnan, et al., "Efficient Distributed Access Control Using Blockchain for Big Data in Clouds", International Conference on Wireless and Mobile Communications (ICWMC), Jun. 30, 2019.

Thwin, et al., "Blockchain-Based Access Control Model to Preserve Privacy for Personal Health Record Systems", Security and Communication Networks, Jun. 25, 2019.

Wang et al., "A Blockchain-Based Framework for Data Sharing with Fine-Grained Access Control in Decentralized Storage Systems," IEEE Access, vol. 6, pp. 38437-38450, Jun. 29, 2018.

Search Report and Written Opinion issued in Appl. No. PCT/AU2020/050844 (2020).

\* cited by examiner

SECURE INFORMATION SHARING SYSTEMS AND METHODS

CROSS-REFERENCE TO RELATED APPLICATIONS

This application is a U.S. nationalization under 35 USC § 371 of International PCT Application No. PCT/AU2020/050844, filed on Aug. 13, 2020, which claims priority from Australian Application No. 2019902918, filed on Aug. 13, 2019, the entirety of which are each fully incorporated by reference here.

TECHNICAL FIELD

Embodiments relate to systems and methods for secure information sharing. In particular, embodiments relate to systems and methods for secure information sharing using distributed ledger or blockchain networks. For example, the information being shared may include sensitive information, such as health related information or medical records.

BACKGROUND

With the proliferation of computing devices and electronic information repositories in everyday life, an exponentially larger volume of data is being generated by every day interactions between humans and interactions between humans and machines. The generated data often includes sensitive, private, commercial or other valuable information that is not intended by the custodians of the data to be publicly or widely accessible. However, most data derive their value if they are accessible by suitably authorised individuals or information systems.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Some embodiments relate to a system for secure information sharing comprising:
  one or more processors; and
  a memory accessible to the one or more processors, the memory comprising executable program code to implement an information sharing engine, the information sharing engine when executed configuring the one or more processors to:
  receive a first request from a data owner device to define a data access key, the first request comprising data access parameters and a data access policy,
  encrypt the data access parameters to generate the data access key based on the data access parameters, wherein the data access parameters enable querying of a system of record to extract data records;
  define a data access control configuration based on the data access policy, the data access control configuration defining data access rights of one or more data consumers;
  transmit to a distributed ledger network a request to store the data access key and the data access control configuration on the distributed ledger network;
  receive a second request to access the data records from a data consumer device, the second request comprising a data consumer identifier;
  responsive to the second request, generate and transmit a third request to access the data records to the distributed ledger network, the third request comprising the data consumer identifier;
  when the third request to access data records is determined to be valid based on the data access control configuration, receiving the data access key from the distributed ledger network and making the received data access key accessible to the data consumer device.

In some embodiments, the data access control configuration is accessible to an access control smart contract implemented on the distributed ledger network.

In some embodiments, the access control smart contract is executable by one or more distributed ledger nodes forming part of the distributed ledger network, each distributed ledger node being a computing system comprising a node processor to execute the access control smart contract and a node memory to store a distributed ledger data structure.

In some embodiments, the validity of the third request is determined based on an output of the access control smart contract and reaching consensus on the output among the distributed ledger nodes.

In some embodiments, reaching consensus among the distributed ledger nodes comprises at least half of the distributed ledger nodes determining a common output of the access control smart contract.

In some embodiments, the information sharing engine when executed configures the one or more processors to:
  receive a fourth request from the data owner device, the fourth request comprising modification instructions to modify the data access policy;
  responsive to receiving the fourth request, modify the data access control configuration based on the modification instructions; and
  transmit to the distributed ledger network a request to store the modified data access control configuration on the distributed ledger network.

In some embodiments, the instructions to modify the data access policy comprise instructions to revoke data access of the data consumer device.

In some embodiments, the information sharing engine is further configured to:
  decrypt the received data access key to determine the data access parameters; and
  on determining validity of the third request, make the decrypted data access parameters accessible to the data consumer device.

In some embodiments, the data access parameters enable authentication through any one of: multi-factor authentication, Security Assertion Mark-up Language (SAML) based authentication or biometric authentication.

In some embodiments, the data records in the system of record comprise data generated by any one or more of a personal fitness device, a wearable device, a smartphone, a tablet, a home automation device, a social media profile or a computer application executing on a computing device.

In some embodiments, the information sharing engine when executed further configures the one or more processors to:

create a data owner account for the data owner, the data owner account comprising a data owner public identifier to publicly identify the data owner and a data owner private identifier, the data owner private identifier not being publicly known; and create a data consumer account for the data consumer, the data consumer account comprising a data consumer public identifier to publicly identify the data consumer and a data consumer private identifier, the data consumer private identifier not being publicly known.

In some embodiments, the data access policy defines restrictions on access to the data access key based on the data consumer identifier.

In some embodiments, the data access policy defines restrictions on access to the data access key based on the data consumer identifier and a time at which the second request is received.

In some embodiments, the information sharing engine further comprises an integration management module that enables the querying of the system of record to extract data records based on the data access parameters.

Some embodiments relate to a data owner device for secure information sharing comprising:
at least one data owner processor;
data owner memory,
the data owner memory comprising executable program code that when executed by the at least one data owner processor configures the at least one data owner processor to:
transmit a first request to an information sharing engine requesting generation of a data access key, the first request comprising data access parameters and a data access policy, wherein the data access parameters enable querying of a system of record to extract data records;
responsive to the first request, receive a response from the information sharing engine, the response comprising the data access key.

Some embodiments relate to a data consumer device for secure information sharing comprising:
at least one data consumer processor;
a data consumer memory,
the data owner memory comprising executable program code that when executed by the at least one data consumer processor configures the at least one data consumer processor to:
transmit a request to an information sharing engine to access data records from a system of record, the request comprising a data consumer identifier;
receiving a data access key from the sharing engine, the data access key being stored on a distributed ledger network;
querying the system of record to extract data records using the data access key.

Some embodiments relate to a computer implemented method for secure information sharing comprising:
receiving a first request from a data owner device to define a data access key, the first request comprising data access parameters and a data access policy,
encrypting the data access parameters to generate the data access key based on the data access parameters, wherein the data access parameters enable querying of a system of record to extract data records;
defining a data access control configuration based on the data access policy, the data access control configuration encoding data access rights of one or more data consumers;
transmitting to a distributed ledger network a request to store the data access key and the data access control configuration on the distributed ledger network;
receiving a second request to access the data records from a data consumer device, the second request comprising a data consumer identifier;
responsive to the second request, generating and transmitting a third request to access the data records to the distributed ledger network, the third request comprising the data consumer identifier;
when the third request to access data records is determined to be valid based on the data access control configuration, receiving the data access key from the distributed ledger network and making the received data access key accessible to the data consumer device.

In some embodiments, the data access control configuration is accessible to an access control smart contract implemented on the distributed ledger network.

In some embodiments, the access control smart contract is executable by one or more distributed ledger nodes forming part of the distributed ledger network, each distributed ledger node being a computing system comprising a node processor to execute the access control smart contract and a node memory to store a distributed ledger data structure.

In some embodiments, the validity of the third request is determined based on an output of the access control smart contract and reaching consensus on the output among the distributed ledger nodes.

In some embodiments, reaching consensus among the distributed ledger nodes comprises at least half of the distributed ledger nodes determining a common output of the access control smart contract.

In some embodiments, the method further comprises:
receiving a fourth request from the data owner device, the fourth request comprising modification instructions to modify the data access policy;
responsive to receiving the fourth request, modify the data access control configuration based on the modification instructions; and transmitting to the distributed ledger network a request to store the modified data access control configuration on the distributed ledger network.

In some embodiments, the instructions to modify the data access policy comprise instructions to revoke data access of the data consumer device.

In some embodiments, the method further comprises: decrypting the received data access key to determine the data access parameters; and on determining validity of the third request, make the decrypted data access parameters accessible to the data consumer device.

In some embodiments, the data access parameters enable authentication through any one of: multi-factor authentication, Security Assertion Mark-up Language (SAML) based authentication or biometric authentication.

In some embodiments, the data records in the system of record comprise data generated by any one or more of a personal fitness device, a wearable device, a smartphone, a tablet, a home automation device, a social media profile or a computer application executing on a computing device.

In some embodiments, the method further comprises:
creating a data owner account for the data owner, the data owner account comprising a data owner public identifier to publicly identify the data owner and a data owner private identifier, the data owner private identifier not being publicly known; and creating a data consumer account for the data consumer, the data consumer account comprising a data consumer public identifier to publicly identify the data consumer and a data consumer private identifier, the data consumer private identifier not being publicly known.

In some embodiments, the data access policy defines restrictions on access to the data access key based on the data consumer identifier.

In some embodiments, the data access policy defines restrictions on access to the data access key based on the data consumer identifier and a time at which the second request is received.

In some embodiments, the method further comprises querying of the system of record to extract data records based on the data access parameters.

Some embodiments relate to a computer-readable storage medium comprising instructions which, when executed by a computer, cause the computer to provide a system for secure information sharing as described herein.

DETAILED DESCRIPTION

Embodiments relate to methods and systems for secure information sharing. In particular, embodiments relate to systems and methods for secure information sharing using distributed ledger or blockchain networks. For example, the information being shared may include sensitive information, such as health related information or medical records. Embodiments may be used by various participants including: data owners, data consumers, and data custodians, for example. The data owners may use the embodiments to securely and controllably share data, including private data, with data consumers. The data consumers may use the embodiments to access data that they have been given permission to access. Data custodians may use the embodiments to securely make data available to data owners and data consumers.

The embodiments provide the capability to allow custodians or owners of data to manage access to their data by consumers of their data through a secure and reliable framework for secure information sharing. The systems and methods according to the embodiments allows links or pointers to information or data to be managed through a distributed ledger or a blockchain network. The systems and methods according to the embodiments allow the management of access privileges or rights to the links or pointers on the distributed ledger network using smart contracts on the distributed network. Key participants in the system and methods are data owners, data custodians and data consumers. A data owner may be an individual, entity or information system that owns data intended for sharing. A data consumer may be an individual, entity or an information system that is interested in accessing data owned by the data owner.

Figure 1:
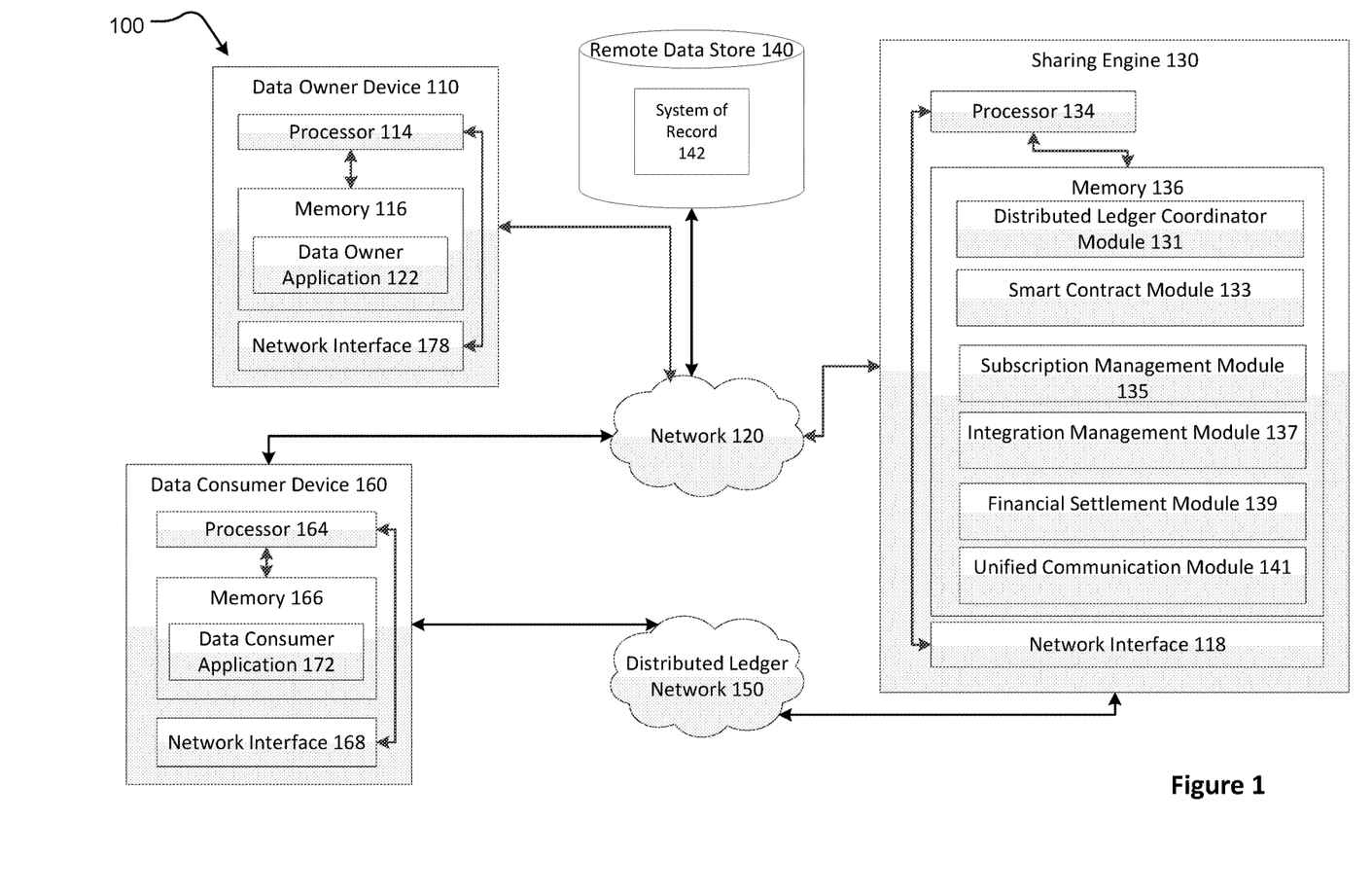
FIG. 1 is a block diagram of a secure information sharing system.

FIG. 1 is a block diagram of an information sharing system 100 according to some embodiments. The information sharing system 100 comprises: a sharing engine 130, one or more data owner devices 110, one or more data consumer devices 160, one or more remote data stores 140, a communication network 120 and a distributed ledger or blockchain network 150. The sharing engine 130 may be implemented in the form of a server or a server system configured with a processor 134 and memory 136 and a network interface 118. Memory 136 may comprise a combination of volatile and non-volatile memory. In some embodiments the sharing engine 130 may comprise more than one processor. The network interface 118 allows the sharing engine 130 to communicate with systems or computing devices external to the sharing engine 130. The network interface 118 may comprise a combination of network interface hardware and software suitable for a relevant communication channel. In some embodiments, the sharing engine may be implemented using more than one server system configured to operate in parallel or using commercially available cloud computing services.

Memory 136 of the sharing engine 130 comprises program code to implement several software modules to provide the information sharing and management capability. The software modules include: a distributed ledger coordinator module 131, a smart contract module 133, a subscription management module 135, and an integration management module 137. The distributed ledger coordinator module 131 performs transactions on the distributed ledger or blockchain network 150. The smart contract module 133 configures smart contracts implemented using the distributed ledger network 150. The subscription management module 135 manages the subscription rights of data owners and data consumers that use the information sharing system 100. The subscription rights may include rights to perform operations using the system and any particular limitations of the operations. The integration management module 137 enables the querying of data or information stored in the remote data store 140 using data access credentials.

The network 120 may include, for example, at least a portion of one or more networks having one or more nodes that transmit, receive, forward, generate, buffer, store, route, switch, process, or a combination thereof, etc. one or more messages, packets, signals, some combination thereof, or so forth. The network 120 may include, for example, one or more of: a wireless network, a wired network, an internet, an intranet, a public network, a packet-switched network, a circuit-switched network, an ad hoc network, an infrastructure network, a public-switched telephone network (PSTN), a cable network, a cellular network, a satellite network, a fiber optic network, some combination thereof, or so forth.

The data owner device 110 comprises one or more processors 114, memory 116 accessible to the one or more processors 114 and a network interface 178 accessible to the one or more processors 114. Memory 116 stores program code implementing a data owner application 122 that allows the data owner to interact with the secure information sharing system 100. Data owner device 110 will typically act as a client device, for example where the sharing engine 130 acts as a server.

The data consumer device 160 comprises one or more processors 164, memory 166 accessible to the one or more processors 164 and a network interface 168 accessible to the one or more processors 164. Memory 166 stores program code implementing a data consumer application 172 that allows the data consumer to interact with the secure information sharing system 100. Data consumer device 160 may act as a client device, for example where the sharing engine 130 acts as a server, although in some instances, the data consumer device 160 may be part of or comprise a server system.

The data consumer device 160 and the data owner device 110 may each be portable and/or personal computing devices, for example, such as smartphones, tablets, laptops, desktop computers or wearable computing devices.

A blockchain or a distributed ledger is a database consisting of two or more block records ("blocks") that are linked together and that adhere to a predetermined standard or protocol. Each block is a data structure that contains a payload and a link to a previous block. However, the link to a previous block may be omitted from the initial block.

According to a conventional blockchain protocol, a block also includes a hash value for the payload and a proof of work (POW), possibly along with other hash values or other types of data. Data items such as the link to the previous block, the POW, and the hash of the payload may be collected into a block header. The payload may include one or more transaction records. For brevity, transaction records may be referred to as "transactions." Each transaction may be timestamped and digitally signed by the participating computing entity which initiated it. After a computing entity initiates a transaction through a distributed ledger node, the distributed ledger node may send it to other blockchain peers via the distributed ledger network 150.

A blockchain may be considered a "distributed" database because multiple different data processing systems may obtain copies of the blockchain, and multiple different nodes or data processing systems (DPSs) or computing devices may update the blockchain. For instance, a blockchain may be made available to a group of data owners and data consumers via the Internet, and the data owners and data consumers may update the blockchain by creating a new block for the end of the blockchain and publishing that block to nodes in the distributed ledger network 150.

A blockchain may include all valid blocks that have ever been created. Accordingly, a blockchain may contain a set of data records that is continuously growing, with each record referring to at least one previous record on the set. A blockchain may thus be hardened against tampering and revision. Contributors to the distributed ledger, such as the sharing engine 130 and other nodes, cooperate to maintain and build the distributed ledger network 150. Each node in the distributed ledger network may include a copy of the entire blockchain or a portion of the blockchain. In some embodiments, the data consumer device 160, the sharing engine 130 and the data owner device 110 may each form a node of the distributed ledger network 150.

The information sharing system 100 provides a reliable, personally controlled method, useable by data owners or custodians, of securing and corralling personal data (PD) and personal records (PR) information that can be selectively accessed and shared to other nominated parties, such as data consumers.

The PD and PR information is owned by an individual, an entity or an information system while inferences derived from the PD and PR may be owned by someone other than the individual, entity or the information system. In several jurisdictions, personal information may be protected from unauthorised access and use via various legal provisions, such as legislation or regulations or directives. The legal provisions regarding protection of personal information may specifically apply to particular contexts, for example personal health or medical data.

The PD and PR may be stored in a number of separate and distinct electronic repositories, databases, file sharing systems, devices and provisioning applications— collectively called system of record (SOR). The term "system of record" or SOR as used herein refers to an information storage system that is an authoritative data source for a given data element or piece of information. Remote Data Store 140 is an example of a repository where one or more SORs in whole or in part may be stored.

Separate SORs may be individually protected by a range of security and access mechanisms including, for example, username/password, multi-factor authentication, Security Assertion Markup Language (SAML) Compliant distributed authentication mechanisms, biometric authentication, which may be used by the individual, and any authorised third parties, in order to access the stored personal data and personal records stored in the SOR and effectively deliver any services which rely upon the information and data contained therein. For example, some of the SOR containing tracked personal activity and health and wellbeing data may be associated with consumer grade devices, such as personal fitness devices, wearables, smartphones, tablets, home automation products and online social media facilities. Data collected by these devices may be locally stored on the devices or remotely contained on platforms hosted in the publicly accessible information systems.

This reliance upon separate and disparate SORs for the collective information contained in the PD/PR places a substantial burden upon individuals to remember the specific security and account information required for them to access the private data contained within the SORs. In addition, the individual's ability to reliably and securely grant access to others to specifically access elements of the data may be cumbersome and error prone and may expose the PDs and PRs to hacking, interception and intrusion— if it can be granted at all. The secure information sharing system 100 advantageously enables more efficient and flexible management of fragmented PD/PR over various SORs.

The secure information sharing engine 100 advantageously provides the following improvements in control and security of the data and information contained in the SORs:

Provisioning access to the nominated SOR without necessarily sharing fundamental security credentials that protects the SOR;

Requiring that data consumers being granted access to an SOR honour access restrictions based on level of access, timeliness of access and revocation of access without recourse to a modification of actual security credentials;

Differentially revoking or modifying access rights of a single data consumer or group of data consumers for a specific SOR without requiring a change to any fundamental security credentials protecting the resource;

Ability to completely remove all granted access rights to any data consumer for a particular SOR based on a single action by the data owner.

The information sharing system 100 facilitates and manages secure information sharing by the use of a blockchain or distributed ledger enabled encryption algorithm and smart contract to intermediate secure sharing of information between the data owner of the personal information in the SOR and data consumers being granted access to the SOR.

The information sharing system 100 may also allow for a data owner to monetise access to the resources that are protected by blockchain encryption by levying a fee for access to the SOR. Such a levy can be applied universally against all smart contracts that are managing access to one or more SORs, or on individual instances where access is granted to specific data consumers. The information sharing system 100 does not expose the primary authentication credential used to protect the SOR as part of the provisioning of access to the party the subject of the access contract.

The various software modules of the sharing engine 130 are configured to be independent modules or application services within the sharing engine 130. This enables modularisation of functionality, which can be enabled or disabled as required based on a data owner's subscription plan.

The subscription management module 135 manages service user registration, user security, user profile maintenance, account linkages, and administrative user management. The subscription management module 135 also manages various functions of subscription management and subscription usage payments. These functions may include, for example: processing initial service subscriptions and service renewal fees; periodic subscription fee calculations; customer account monitoring and usage fee generation; determining fees applicable to data consumers based on usage; determining fees applicable to data owners based on usage; and starting, suspending, resuming and stopping access to the secure information sharing system 100.

The financial settlement module 139 manages: the generation of financial institution charges for registered subscribers or data owners or data consumers; payment of 'fee for service' usage when configured for a subscriber; generation of 'fee for services' charges for users of the service; and sending and receiving financial institution documents to facilitate settlement of financial transactions. The integration management module 137 manages requests from data owners to either start, suspend, resume or stop an integration service associated with their SOR 142.

The unified communication module 141 facilitates the interactions between the various data owner subscribers and data consumer subscribers and one or more remote data stores 140 for all communication performed other than the use of the encryption APIs for secure information communication. The unified communication module 141 is designed to allow email, SMS or notification messages to be generated and routed to subscribers for alerting of events and alarms that may be generated from the integration management module 137 from time to time.

The integration management module 137 provides callable interfaces that may be invoked by the data owner device 110 or the data consumer device 160 to create, publish and allow access to links or pointers to securely access the system of record 142. The integration management module 137 comprises algorithms and program code that facilitates communication with the distributed ledger network 150.

The distributed ledger network 150 supports inclusion of access control program code in its ledger shared across all the nodes of the distributed ledger network. The access control program code, also known as a smart contract, is executable over the distributed ledger network 150 using a distributed ledger specific virtual machine. The smart contract may be used to enforce specific logic on transactions performed over the distributed ledger network. Examples of suitable distributed ledger protocols include Ethereum, Hyperledger, Corda, Chain, and Ripple.

The data owner device 110 may transmit a request to the sharing engine 130 to request access to the distributed ledger network 150 using the data owner's private account (configured with a username and a password). The data owner device 110 through the transmitted request to the sharing engine 130 enables configuration of a link or a pointer to the system of record 142.

In order to share a system of record 142, the data owner device 110 transmits a request to the sharing engine 130 to create a key or a link or a pointer to the system of record 142. The request may comprise the data owner's unique subscription code created by the subscription management module 135, along with the necessary resource attributes to uniquely identify the system of record 142.

The sharing engine 130 may validate the subscription code with the subscription management module 135. If the subscription code is found to be valid then the sharing engine 130, through the distributed ledger coordinator module 131 transmits a record creation request to the distributed ledger network 150, the record creation request including all necessary elements for the user's request to secure the resource.

In some embodiments, the distributed ledger coordinator module 131 may invoke or call the smart contract module 133 to determine if there are any defined conditions associated with the data owner's subscription that place specific predefined access conditions on the sharing of the system of record 142.

The distributed ledger network may return a blockchain or distributed ledger reference to the distributed ledger coordinator module 131. The distributed ledger coordinator module 131 may wait for consensus from at least 50% of the nodes of the distributed ledger network 150 and then provide the blockchain or distributed ledger reference to the integration management module 137. In some embodiments, the integration management module 137 may transmit the blockchain or distributed ledger reference to the remote data store 140.

When a data owner intends to share a record that forms part of the system of record 142 with a data consumer, the data owner device 110 may do so by transmitting the blockchain or distributed ledger reference to the integration management module 137 and invoke a "Publish Key" request. The "Publish Key" request initiates transmission of the blockchain or distributed ledger reference to the data consumer device 160.

On a request for access to the system of record 142 being sent by the data consumer device 160 to the sharing engine 130, the blockchain or distributed ledger reference held by the data consumer device 160 is validated by the subscription management module 135 to ensure that the subscription service for the SOR owner is valid. If the subscription is determined to be valid, the distributed ledger coordinator module 131 decrypts the supplied blockchain or distributed ledger reference and returns a validated key and access instruction to the data consumer device 160, which then accesses the remote data store 140 and securely reads one or more records in the system of record 142.

Figure 2:
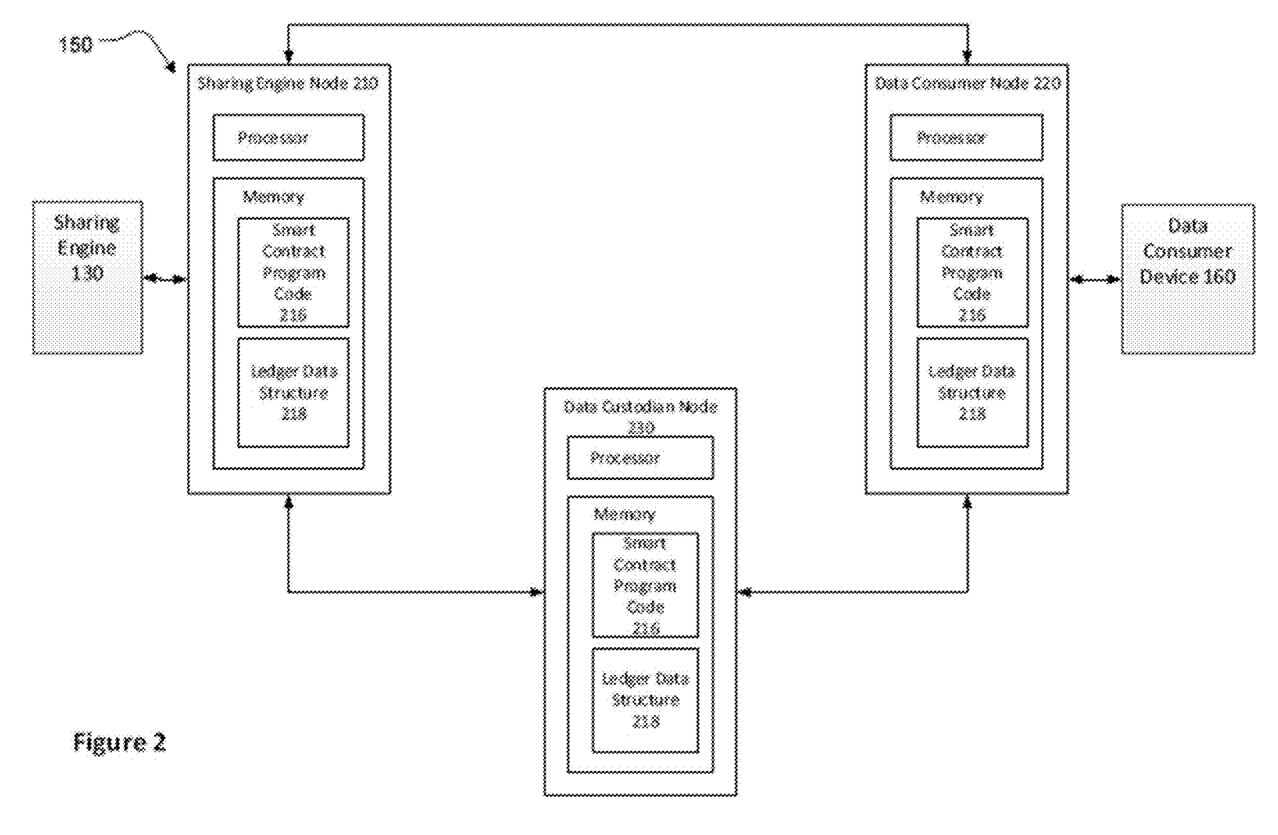
FIG. 2 is a block diagram of part of a distributed ledger network.

FIG. 2 illustrates part of the distributed ledger network 150 showing some of the nodes forming the distributed ledger network 150. Each of the nodes may be controlled by a separate entity or organisation. The separate entities or organisations come together through the distributed ledger network 150 to collectively administer secure information sharing using a common information sharing blockchain protocol. The information sharing blockchain protocol defines the various relevant parameters for inter-node communication, block structure, applicable cryptographic algorithms for transaction verification, and relevant conditions for reaching consensus across the network, for example.

The distributed ledger network 150 may comprise at least one sharing engine node 210, at least one data consumer node 220, at least one data custodian node 230, for example. Each node in the distributed ledger network 150 stores a copy of the ledger data structure 218 and smart contract program code 216. The ledger data structure 218 comprises a record of all the transactions performed over the distributed ledger network 150. The recorded transactions may include: creation of a new link or reference to a system of record 142 by the data owner device 110, granting of access to a system of record 142, revoking of access to a system of record 142, accessing the credentials stored in a link or reference to a system of record 142 on the ledger data structure 218, for example. Other relevant transactions for facilitating secure sharing of information may be performed over the distributed ledger network 150. The smart contract program code 216 encodes the logic or instructions for execution of the transactions over the distributed ledger network 150.

Any one of the nodes of the distributed ledger network 150 may initiate a specific transaction by sending a message including parameters for the transaction to all other nodes of the distributed ledger network 150. Once a transaction is submitted, the nodes of the distributed ledger network 150 verify the transaction by executing their respective copies of the smart contract program code 216. After verification of the transaction, the respective nodes of the distributed ledger network 150 attempt to reach a consensus by following the information sharing blockchain protocol that defines the conditions for reaching consensus. Various algorithms used in distributed computing for reaching consensus may be used, including: voting based consensus algorithm, or lottery based consensus algorithm, or proof of work based consensus algorithm, or proof of stake based consensus algorithm, or proof of authority based consensus algorithm, for example. Once consensus is reached across the network, all the nodes update the ledger data structure 218 with the details of the new transaction. The details of the new transaction are based on the transaction parameters entered when a transaction is initiated and the result produced by execution of the smart contract program code 216.

Figure 3:
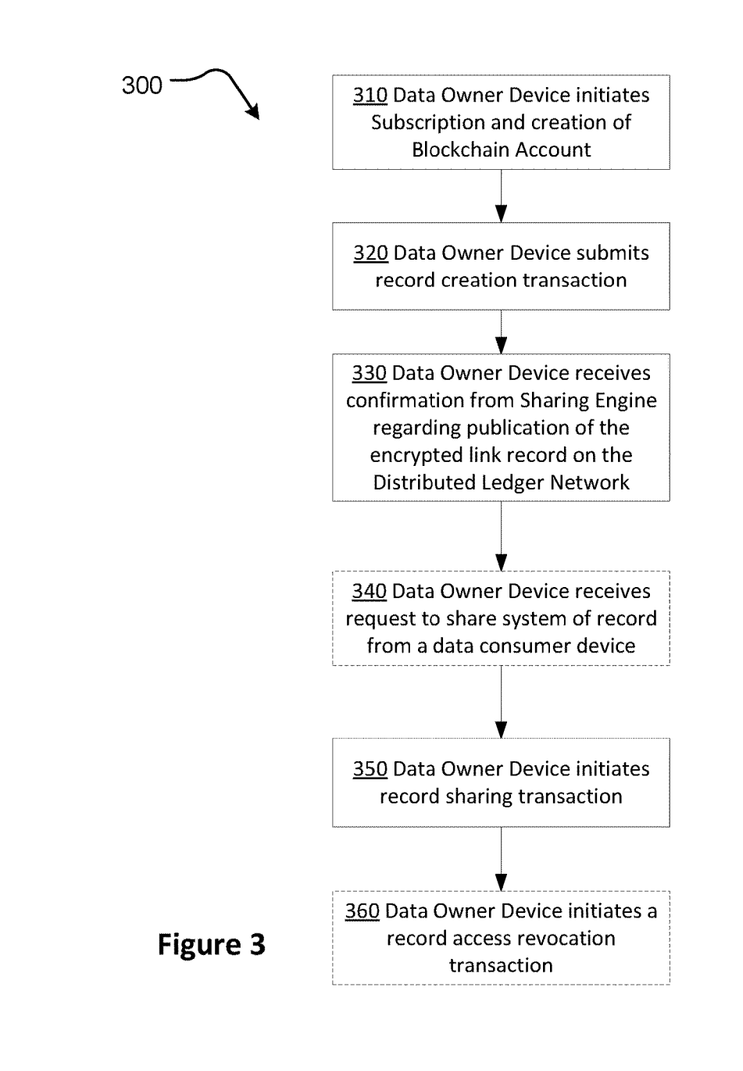
FIG. 3 is flowchart of a series of steps performed by a data owner device.

FIG. 3 is a flowchart of a method 300 comprising a series of steps performed by the data owner device 110 according to some embodiments. At step 310, the data owner device 110 initiates a subscription with the sharing engine 130. As part of this step, unique private and public keys are created for the data owner's subscription account. The private key is held by the data owner and allows the data owner to include digital signatures in transactions initiated by the data owner. The public key is a public identifier for the data owner. The public key is used by the various nodes of the distributed ledger network 150 to determine the identity of the initiator of a transaction.

At step 320, the data owner initiates a record creation transaction to create an encrypted link record that refers to the system of record 142 that the data owner owns. The encrypted link record comprises information necessary for accessing the data stored in the system of record 142. This may include access credentials, or IP (internet protocol) addresses, for example. The record creation transaction is submitted to the distributed ledger network 150 through the distributed ledger co-ordinator module 131. Once the record creation transaction is submitted to the distributed ledger network 150, the smart contract program code 216 is executed by the various nodes of the distributed ledger network to verify the transaction. If the transaction is verified as valid, the encrypted link record is included in the ledger data structure 218. Although the ledger data structure 218 is accessible to all members of the node, because the link record is encrypted, members having access to the encrypted link record will not be able to access the system of record 142 because the necessary information to access the system of record 142 is not surmisable from the encrypted link record.

If the transaction submitted at step 320 is successfully verified by the distributed ledger network 150 by reaching consensus, then at step 330, the data owner device 110 receives a confirmation of the successful publication of the encrypted link record on the distributed ledger network 150. Step 340 is an optional step where a data owner device 110 receives an access request from a data consumer device 160 for access to a specific system of record 142. The access request includes an identifier, such as a public key of the data consumer enabling the data owner to verify the validity of the request. If the data owner agrees to the data consumer's request, then at step 350, the data owner device 110 initiates a record sharing transaction to share the encrypted link record (record sharing transaction or access grant transaction). The record sharing transaction is submitted to the distributed ledger network 150 by the distributed ledger co-ordinator module 131. The transaction parameters include the public key of the data consumer, an identifier of the encrypted link record, the public key of the data owner and the data owner's digital signature. The record sharing transaction is executed by one or more nodes of the distributed ledger network 150 by providing the parameters to the smart contract program code 216. On execution of the smart contract program code 216, if the transaction is validated and consensus amongst the nodes of the distributed ledger network 150 is reached, then the ledger data structure 218 is updated to reflect the successful granting of access to the encrypted link record to the data consumer device 160 requesting access to the encrypted link record.

Some embodiments may include an optional step of revoking access to a shared encrypted link record. At step 360, a data owner device 110 may initiate a record access revocation transaction to revoke access to a shared encrypted link record. The transaction may be initiated using parameters including the unique identifier of the shared encrypted link record and the public key of the data consumer whose access is intended to be revoked. The record access revocation transaction is submitted to the distributed ledger network 150 by the distributed ledger coordinator module 131 and after the transaction is verified by reaching a consensus on the distributed ledger network 150, the ledger data structure 218 may be updated to reflect the revocation of access to the encrypted link record.

Figure 4:
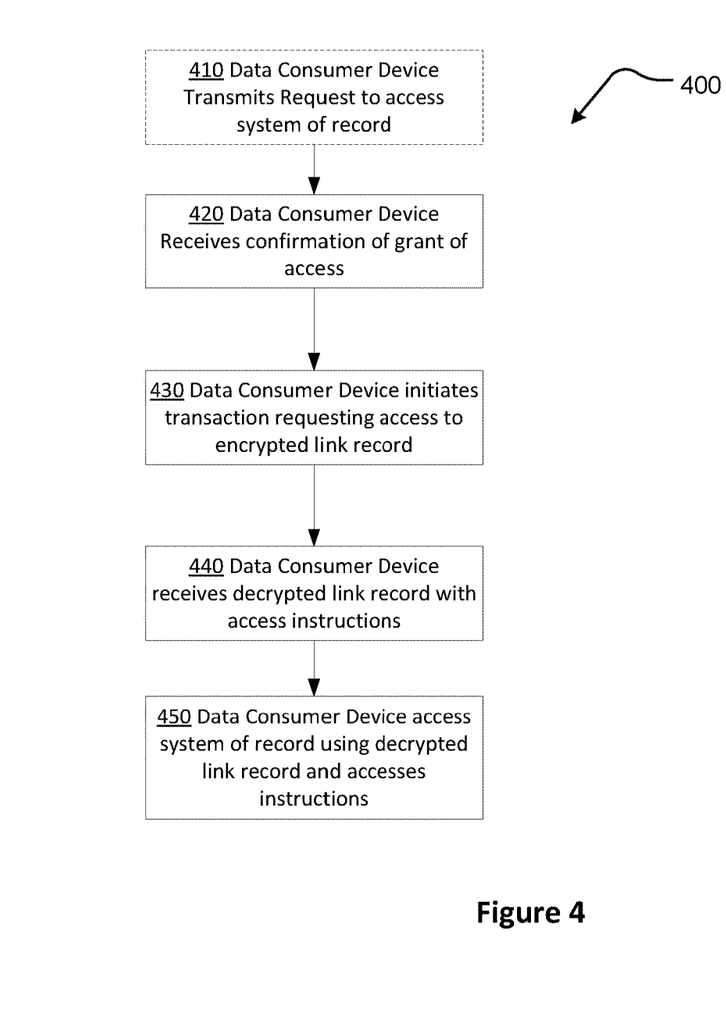
FIG. 4 is flowchart of a series of steps performed by a data consumer device.

FIG. 4 is a flowchart of a method 400 comprising a series of steps performed by a data consumer device 160 to access the system of record 142. Step 410 is an optional step wherein the data consumer device 160 transmits an access request to access the system of record 142 accessible through an encrypted link record published on the distributed ledger network 150. The access request may be transmitted as a request access transaction through the distributed ledger network 150. The request access transaction may include parameters of the public key of the data consumer and a unique identifier of the encrypted link record. On validation of the access request transaction by the distributed ledger network 150, the sharing engine 130 may transmit a notification to data owner device 110 regarding the request for access. Validation of the access request by the distributed ledger network 150 may comprise search or identification of a pre-existing record sharing transaction initiated by the data owner device 110 corresponding to the system of record 142 associated with the encrypted link record. If a corresponding record sharing transaction is identified in the distributed ledger network 150, then the access request transaction may be validated by the distributed ledger network 150.

At step 420, the data consumer device 160 receives confirmation that it has been granted access to an encrypted link record stored on the ledger data structure 218. The confirmation may be received from a data consumer node 220. At step 430, the data consumer device 160 initiates a transaction requesting access to an encrypted link record (access link record transaction). The transaction may be submitted to the distributed ledger network 150 through the distributed ledger coordinator module 131. In an alternative embodiment, the transaction may be submitted to the distributed ledger network 150 through the data consumer node 220. If the access link record transaction is validated based on a pre-existing record sharing transaction corresponding to the encrypted link record, then at step 440, the data consumer device 160 receives a decrypted link record with access instructions from the distributed ledger network 150. The communication of the decrypted link record and access instructions may be intermediated through the sharing engine 130 in some embodiments. Using the decrypted link record and access instructions received at step 430, the data consumer device 160 securely accesses the system of record 142 at step 450.

Figure 5:
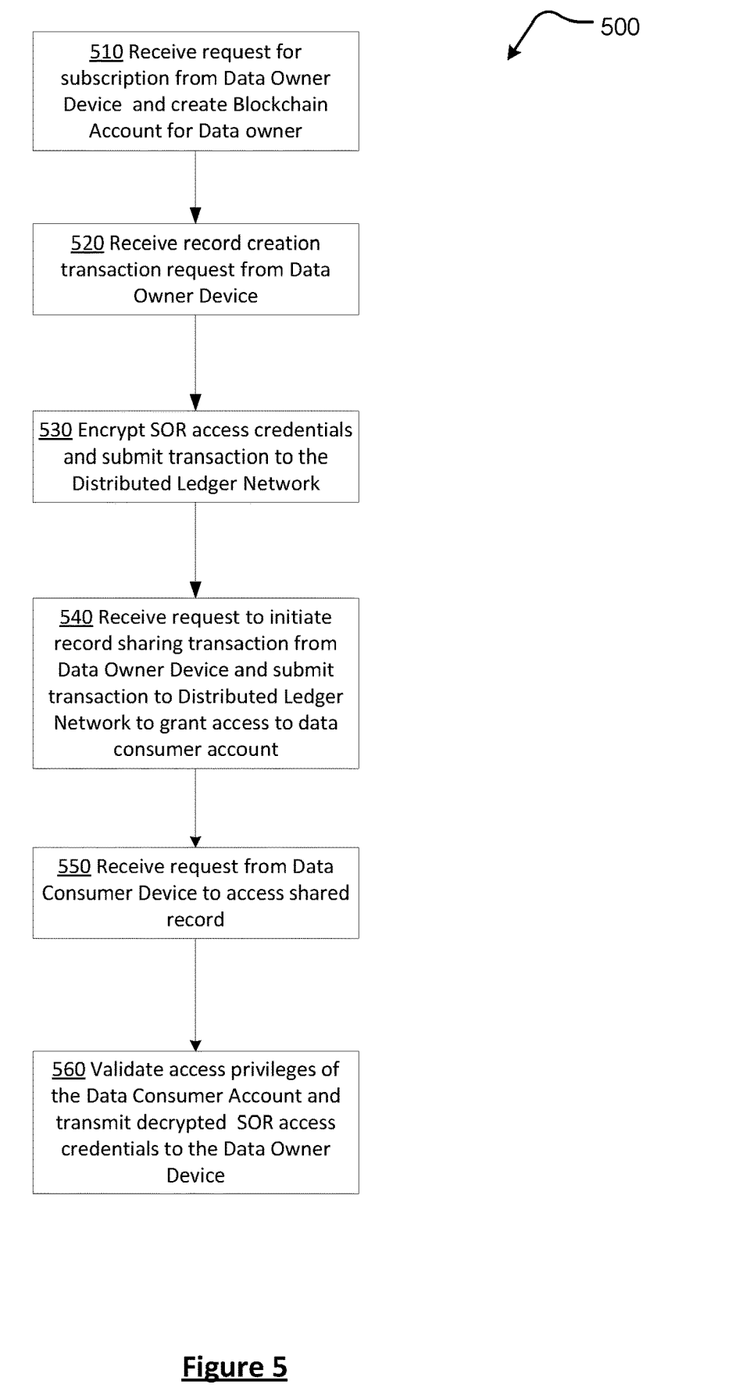
FIG. 5 is flowchart of a series of steps performed by an information sharing engine.

FIG. 5 illustrates a flowchart of a method 500 comprising a series of steps performed by the sharing engine 130 during the secure information sharing process. At step 510, the sharing engine 130 receives a request from a data owner device 110 for initiating a subscription with the secure information sharing system 100. In response to the request, the sharing engine 130 creates an account for the data owner. The account comprises a public data owner key and a private data owner key as a key pair. Both private and public keys are randomly generated. The public key serves as a public identifier of the data owner. The private key is only held by the data owner and allows the data owner to verify the authenticity of the messages it sends by including a signature generated using the private key.

At step 520, the sharing engine 130 receives a request from the data owner device 110 to create a record on the distributed ledger network 150, the record corresponding to a link to a particular system of record 142 comprising the information that the data owner intends to securely share. The request from the data owner device 110 comprises access credentials, IP addresses or other relevant information necessary to access the system of record 142. At step 530, the sharing engine 130 encrypts the information necessary to access the system of record 142 to obtain an encrypted link record. The sharing engine 130 also submits a transaction to the distributed ledger network 150 to include the encrypted link record on the ledger data structure 218. If the transaction is validated by the distributed ledger network 150 by reaching consensus, then the encrypted link record is successfully included in the ledger data structure 218.

At step 540, the sharing engine 130 receives a request from a data owner device 110 to initiate a record sharing transaction with an identified data consumer account associated with a particular data consumer device 160. In response to the record sharing request, the sharing engine 130 initiates a record sharing transaction to grant access to the identified data consumer account. Once the transaction is validated by the smart contract program code 216, the ledger data structure 218 is updated to reflect the granting of access to the data consumer account. Access is granted to a specific encrypted link record previously included in the ledger data structure 218.

At step 550, the sharing engine 130 receives a request from a data consumer device 160 to access a system of record 142 through an encrypted link record included in the ledger data structure 218. In response to the request, at step 560, the sharing engine 130 submits an access validation request to the distributed ledger network 150. If the distributed ledger network 150 reaches consensus on the validity of the access validation request in response to the access validation request, then the sharing engine retrieves the encrypted link record from the ledger data structure 218. After retrieving the encrypted link record, the sharing engine 130 decrypts the link record to obtain the various access parameters, such as credentials and IP Address, for example. The decrypted link record is made available to the data consumer device 160, thereby enabling the data consumer device 160 to directly query the system of record 142.

Figure 6:
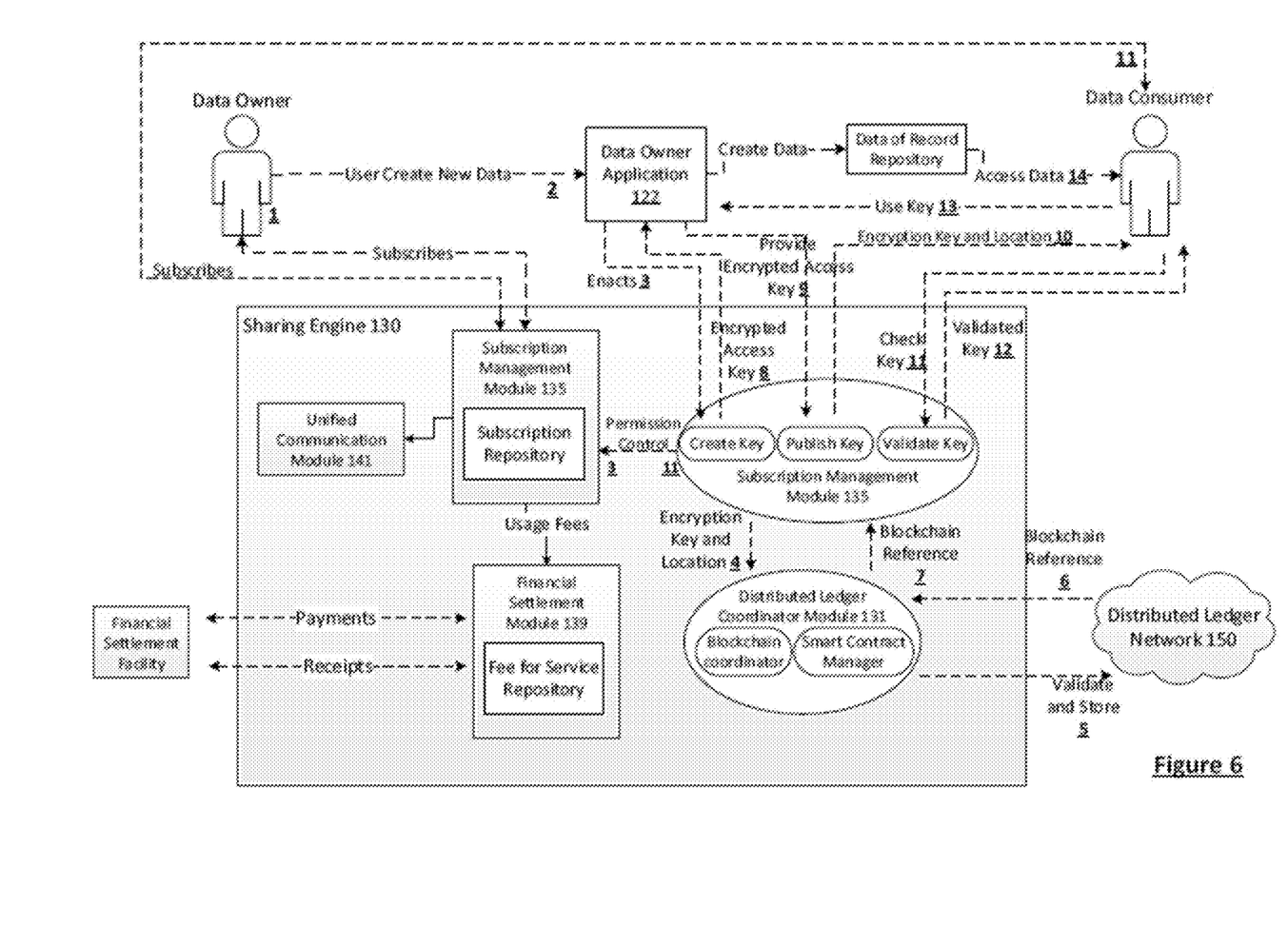
FIG. 6 is a schematic diagram of a secure information sharing system.

FIG. 6 illustrates a schematic diagram according to some embodiments of some of the components of the secure information sharing system 100 and some of the steps performed by the secure information sharing system 100. At step 1, a data owner (Database of Record (DOR) Owner) initiates a subscription through the subscription management module 135 of the sharing engine 130. At step 2, the data owner may create one or more records in a system of record 142. At step 3, the data owner initiates the sharing of the system of record 142 by submitting a record sharing request to the sharing engine 130. At step 4, the sharing engine 130 initiates an encrypted link record creation transaction through the distributed ledger coordinator module 131. At step 5, a record creation transaction is submitted to the distributed ledger network 150. Once consensus is reached within the distributed ledger network, a blockchain reference or a unique identifier of the encrypted link record is received by the sharing engine 130 at step 6. The unique identifier of the encrypted link record is communicated across the various modules of the sharing engine 130 at step 7. At step 8, the unique identifier of the encrypted link record is communicated to the data owner device 110.

At step 9, the data owner device 110 transmits an encrypted access key to the sharing engine 130. At step 10, the encrypted access key received at step 9 along with a location of the system of record 142 is transmitted by the sharing engine 130 to the data consumer device 160. At step 11, the data consumer device 160 submits a request to the sharing engine 130 to validate the received encrypted access key. At step 12, the data consumer device 160 receives a validated key from the sharing engine 130. In alternative embodiments, the verification of the access key may occur by a request to a data consumer node 220. As part of the validation process, the $3^{rd}$ party or the data consumer device 160 may receive a decrypted link record which may comprise information necessary to access the system of record, for example access credentials or IP address of the system of record 142. At step 13, the data consumer device 160 uses the validated key to request access to data records stored in the system of record 142. At step 14, the data consumer device 160 receives data records stored in the system of record 142.

In some embodiments, the secure information sharing system 100 may be used to share health related records such as medical test results, doctor's reports, and any other health related information. The records may be shared by a patient with a medical practitioner or a researcher, for example. The records may be alternatively shared with an entity such as a healthcare provider, insurer or a research institute, for example. In some embodiments, the health related records include data generated from personal health devices such as fitness trackers, weighing scales, thermometers, blood pressure monitors, for example. The records may also include data records generated by a computer application executing on a computing device controlled by an individual. The computer application may include a smart phone application or another bespoke software application, commonly called an "app", such as an application executable using an Android™ or iOS™ operating system. Examples of such apps include apps for self-reporting mental wellbeing of an individual or an app for tracking physical activity such as exercises.

FIGS. 7A, 7B, 7C, 8A, 8B, 8C, 9A, 9B and 9C illustrate screenshots of the data owner application 122 in an embodiment where the data owner device 110 is a smartphone and the data owner application 122 is a smartphone application. Screenshot 710 illustrates a home interface of the data owner application 122 that enables a data owner to navigate through application features. The application features enable data owners to: manage details of their account, manage records they own including documents, manage external systems of record 142 that they have access to, and manage information regarding their lifestyle, body, mind or family, for example. The home interface of screenshot 710 comprises several selectable interactive icons that allow the user to interact with the various functional components of the data owner application 122. For example, clicking or tapping on a personal info icon 712 allows the data owner to manage their personal information. Clicking or tapping on a "my body" icon 711 allows the data owner to manage information regarding their body, such as weight or height or other personal physical information. Similarly, clicking or tapping on a family icon 713 allows the data owner to manage details of one or more of their family member and a personal documents icon 715 allows the data owner to manage documents or access to documents related to their personal information or health. A personal health record icon 718 allows the data owner to enable interaction with an external source or store of information or documents related to their health record.

Figure 7A:
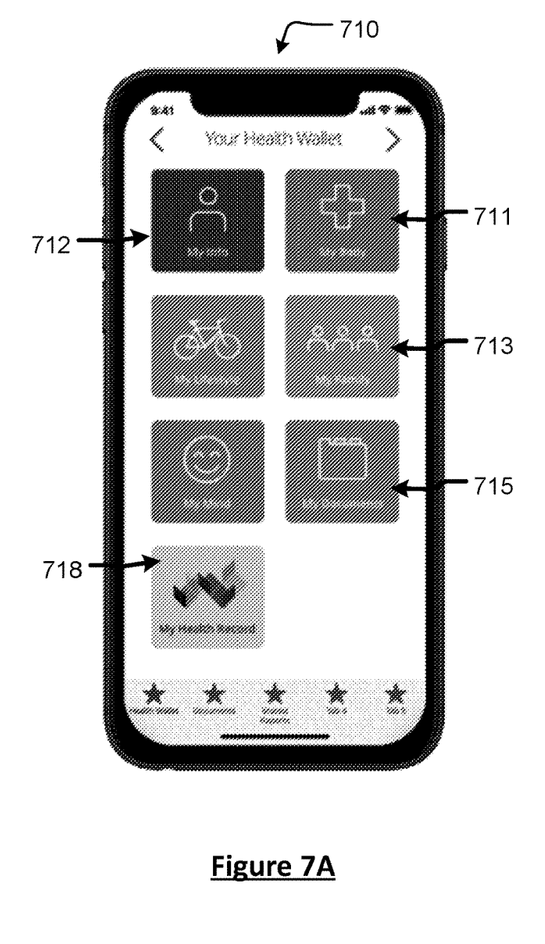
FIG. 7 illustrates screenshots of a data owner application.
Figure 7B:
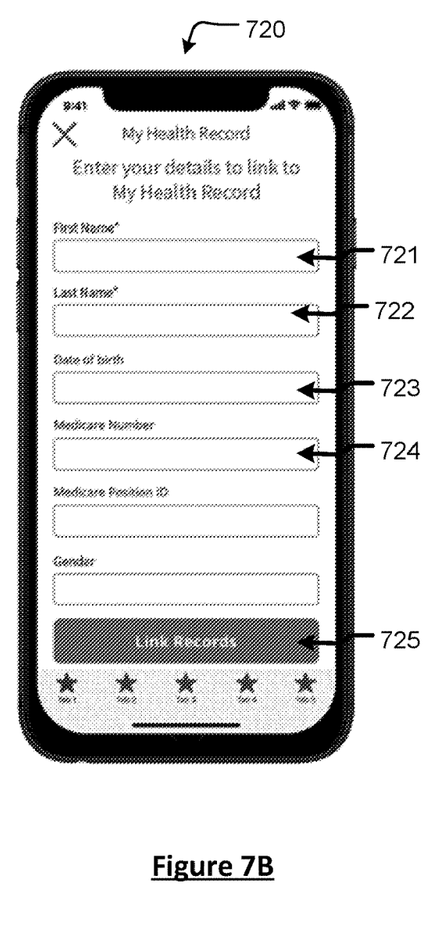

Screenshot 720 illustrates an interface that enables linking a remote data store 140 with the data owner's account. The remote data store 140 may comprise health records in the system of record 142. The data owner may populate linking information such as their first and last name (fields 721 and 722), date of birth (field 723), and a unique identifier associated with their health records (field 724). After populating all the necessary fields, for example as illustrated in screenshot 720, the data owner may initiate the linking process by selecting (e.g. clicking on) the link records button 725.

Figure 7C:
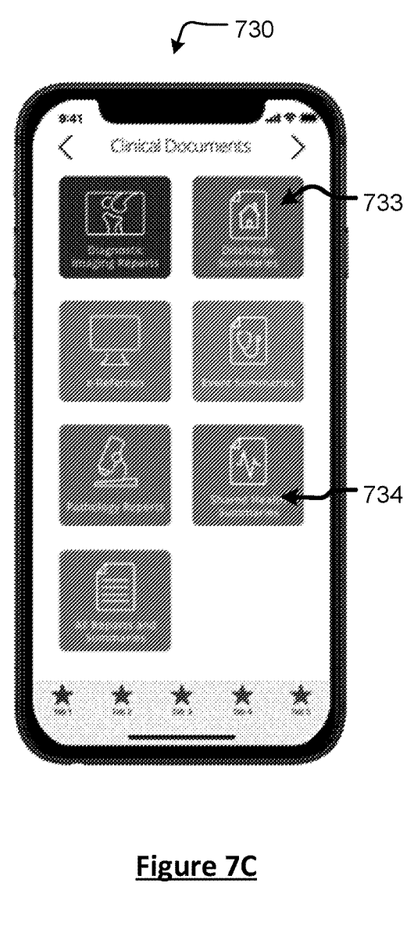
Figure 8A:
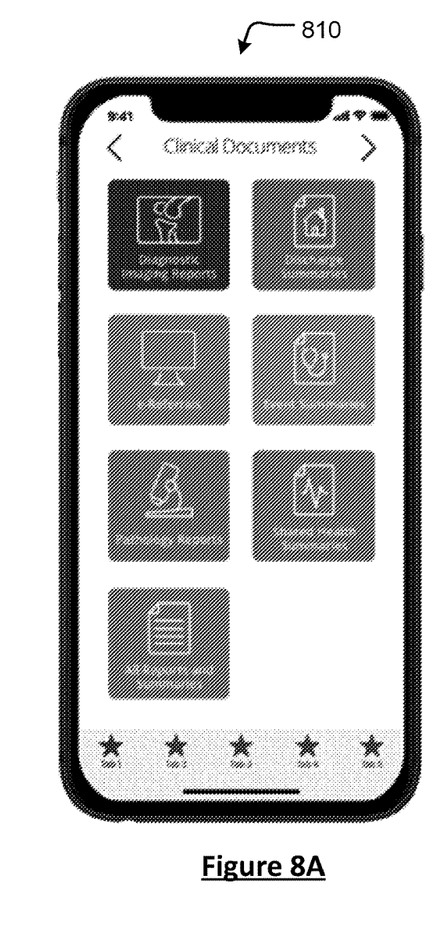
FIG. 8 illustrates further screenshots of the data owner application.
Figure 8B:
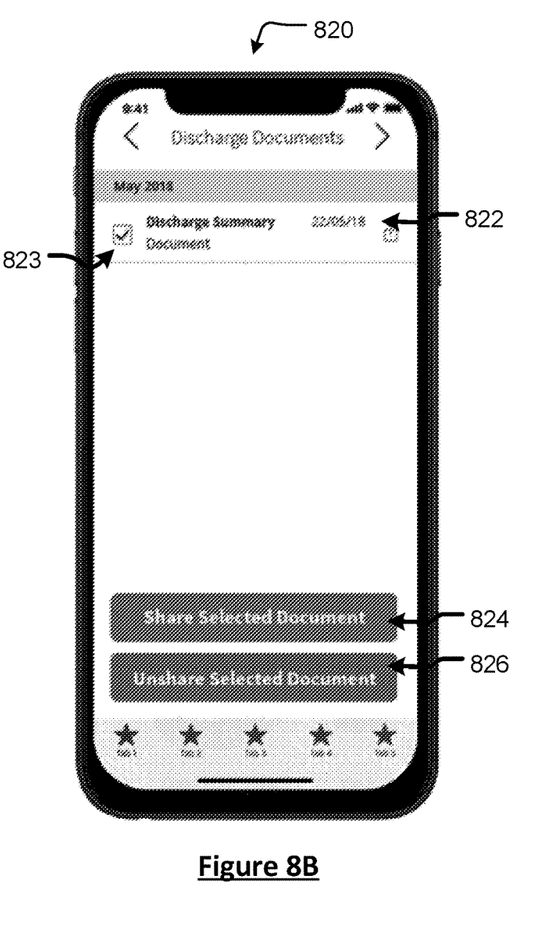
Figure 8C:
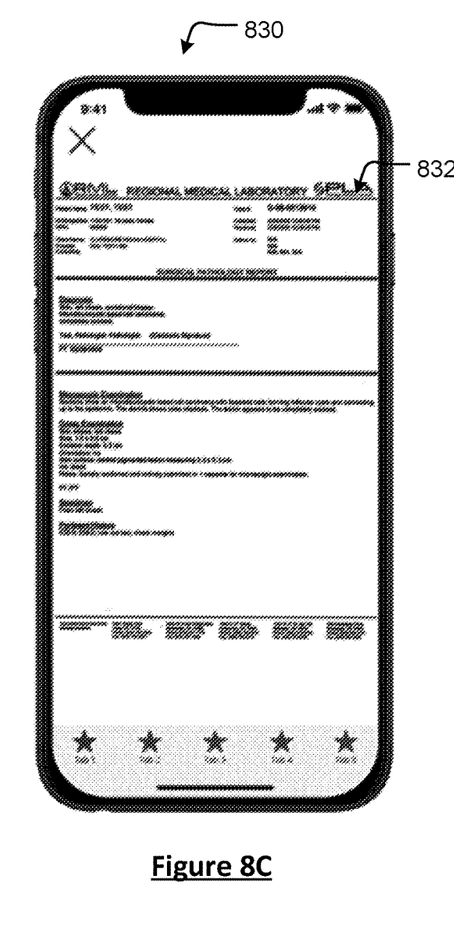

Screenshot 730 illustrates an interface listing various categories of documents capable of being shared through the data owner application 122. For example, clicking or tapping on icon 733 may allow the data owner to share discharge summary documents. Clicking or tapping on a shared health summaries icon 734 may allow a data owner to see a summary of documents previous shared by the data owner.

Similarly, screenshot 810 illustrates an interface that enables selection from among the various categories of records or clinical documents available to the data owner for sharing. Screenshot 820 shows an interface that enables the data owner to select a specific document, such as a discharge summary, for sharing. The sharing action may be responsive to a request share a record received by the data owner device 110 according to step 340 of flowchart 300 of FIG. 3. A document list region 822 in the interface shown in screenshot 820 shows a specific discharge summary document and ticking a checkbox or other selectable user interface component 823 allows the data owner to perform specific sharing operations with one or more selected document in the document list region 822. Clicking or tapping on a share documents button 824 allows a data owner to share one or more selected documents. The sharing action may be performed by the data owner device 110 as described with respect to step 350 of flowchart 300 of FIG. 3. Clicking or tapping on un-share button 826 allows a data owner to un-share or revoke access to one or more shared documents. The un-sharing action may be performed by the data owner device 110 as described with respect to step 360 of flowchart 300 of FIG. 3. Screenshot 830 illustrates an interface that enables a data owner to visualise a preview 832 of a document before sharing.

Figure 9A:
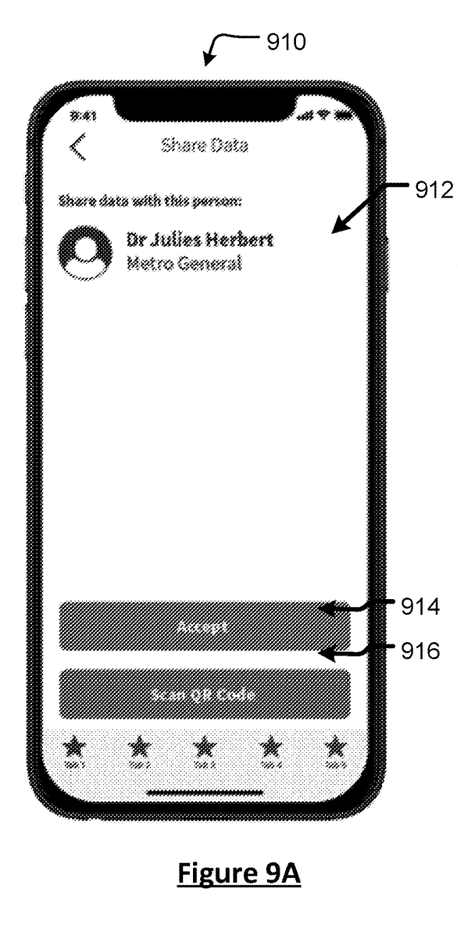
FIG. 9 illustrates further screenshots of the data owner application.

Screenshot 910 illustrates an interface that enables a data owner to review details of a data consumer before sharing the system of record 142 with the data consumer. Region 912 comprises identity information of a data consumer for verification by a data owner before sharing the system of record 142. The identity information may include a name of the data consumer and any other unique identifier necessary to uniquely identify the data consumer. By clicking or tapping on button 914 the data owner may accept the details of the data consumer presented in region 912 and initiate sharing the system of record 142 with the identified data consumer. Alternatively by clicking or tapping on button 916 the data owner may initiate extraction of details of a data consumer by scanning a QR code using a camera provided on the data owner device 110.

Figure 9B:
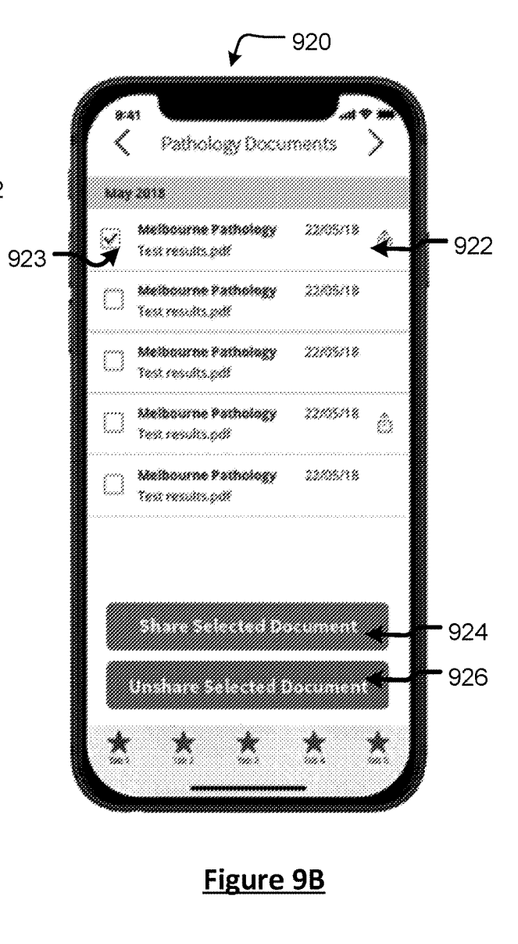
Figure 9C:
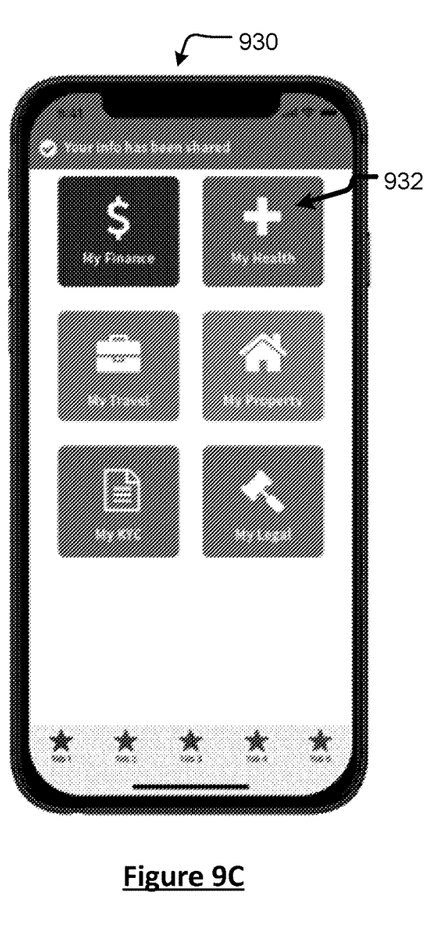

Screenshot 920 illustrates an interface that enables a data owner to select one or more documents or systems of record for sharing with the data consumer selected in screenshot 910. A selectable document region 922 may display details of a document to identify its content or nature. By clicking or tapping on a checkbox 923 the data consumer may select a specific document for a sharing operation. By clicking or tapping on button 924 the data owner my share one or more selected document. The sharing action may be performed by the data owner device 110 as described with respect to step 350 of flowchart 300 of FIG. 3. By clicking or tapping on button 926 the data owner my un-share or revoke access to one or more selected document. The un-sharing action may be performed by the data owner device 110 as described with respect to step 360 of flowchart 300 of FIG. 3. Screenshot 930 illustrates a home screen of the data owner application 122 with a message presented in region 932 confirming the successful sharing of one or more documents or records selected in screenshot 920.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A system for secure information sharing comprising:
one or more processors; and
a memory accessible to the one or more processors,
the memory comprising executable program code to implement an information sharing engine, the information sharing engine when executed configures the one or more processors to:
receive a first request from a data owner device to define a data access key, the first request comprising data access parameters and a data access policy,
create a data owner account for a data owner associated with the data owner device, the data owner account comprising a data owner public identifier to publicly identify the data owner and a data owner private identifier, the data owner private identifier not being publicly known;
encrypt the data access parameters to generate the data access key based on the data access parameters, wherein the data access parameters enable querying of a system of record to extract data records;
define a data access control configuration based on the data access policy, the data access control configuration defining data access rights of one or more data consumers;
transmit to a distributed ledger network a request to store the data access key and the data access control configuration on the distributed ledger network;
receive a second request to access the data records from a data consumer device, the second request comprising a data consumer identifier;
create a data consumer account for a data consumer associated with the data consumer device, the data consumer account comprising a data consumer public identifier to publicly identify the corresponding data consumer and a data consumer private identifier, the data consumer private identifier not being publicly known;
responsive to the second request, generate and transmit a third request to access the data records to the distributed ledger network, the third request comprising the data consumer identifier;
when the third request to access data records is determined to be valid based on the data access control configuration, receiving the data access key from the distributed ledger network and making the received data access key accessible to the data consumer device.

2. The system of claim 1, wherein the data access control configuration is accessible to an access control smart contract implemented on the distributed ledger network, wherein the access control smart contract is executable by one or more distributed ledger nodes forming part of the distributed ledger network,
each distributed ledger node being a computing system comprising a node processor to execute the access control smart contract and a node memory to store a distributed ledger data structure.

3. The system of claim 2, wherein the validity of the third request is determined based on an output of the access control smart contract and reaching consensus on the output among the distributed ledger nodes.

4. The system of claim 1, wherein the information sharing engine when executed further configures the one or more processors to:
receive a fourth request from the data owner device, the fourth request comprising modification instructions to modify the data access policy;
responsive to receiving the fourth request, modify the data access control configuration based on the modification instructions; and
transmit to the distributed ledger network a request to store the modified data access control configuration on the distributed ledger network.

5. The system of claim 4, wherein the instructions to modify the data access policy comprise instructions to revoke data access of the data consumer device.

6. The system of claim 1, wherein the information sharing engine when executed further configures the one or more processors to:
decrypt the received data access key to determine the data access parameters; and
on determining validity of the third request, make the decrypted data access parameters accessible to the data consumer device.

7. The system of claim 1, wherein the data access parameters enable authentication through any one of: multi-factor authentication, Security Assertion Mark-up Language (SAML) based authentication or biometric authentication.

8. The system of claim 1, wherein the data records in the system of record comprise data generated by any one or more of a personal fitness device, a wearable device, a smartphone, a tablet, a home automation device, a social media profile or a computer application executing on a computing device.

9. The system of claim 1, wherein the data access policy defines restrictions on access to the data access key based on one or more of: the data consumer identifier; and a time at which the second request is received.

10. A computer implemented method for secure information sharing comprising:
receiving a first request from a data owner device to define a data access key, the first request comprising data access parameters and a data access policy;
creating a data owner account for a data owner associated with the data owner device, the data owner account comprising a data owner public identifier to publicly identify the data owner and a data owner private identifier, the data owner private identifier not being publicly known;
encrypting the data access parameters to generate the data access key based on the data access parameters, wherein the data access parameters enable querying of a system of record to extract data records;
defining a data access control configuration based on the data access policy, the data access control configuration encoding data access rights of one or more data consumers;
transmitting to a distributed ledger network a request to store the data access key and the data access control configuration on the distributed ledger network;
receiving a second request to access the data records from a data consumer device, the second request comprising a data consumer identifier;
creating a data consumer account for a data consumer associated with the data consumer device, the data consumer account comprising a data consumer public identifier to publicly identify the data consumer and a data consumer private identifier, the data consumer private identifier not being publicly known;
responsive to the second request, generating and transmitting a third request to access the data records to the distributed ledger network, the third request comprising the data consumer identifier;

when the third request to access data records is determined to be valid, based on the data access control configuration, receiving the data access key from the distributed ledger network and making the received data access key accessible to the data consumer device.

11. The computer-implemented method of claim 10, wherein the data access control configuration is accessible to an access control smart contract implemented on the distributed ledger network, wherein the access control smart contract is executable by one or more distributed ledger nodes forming part of the distributed ledger network, each distributed ledger node being a computing system comprising a node processor to execute the access control smart contract and a node memory to store a distributed ledger data structure.

12. The computer-implemented method of claim 11, wherein the validity of the third request is determined based on an output of the access control smart contract and reaching consensus on the output among the distributed ledger nodes.

13. The computer-implemented method of claim 10, wherein the computer-implemented method further comprises:

receiving a fourth request from the data owner device, the fourth request comprising modification instructions to modify the data access policy;

responsive to receiving the fourth request, modify the data access control configuration based on the modification instructions; and transmitting to the distributed ledger network a request to store the modified data access control configuration on the distributed ledger network.

14. The computer-implemented method of claim 10, wherein the computer-implemented method further comprises:

decrypting the received data access key to determine the data access parameters; and on determining validity of the third request, make the decrypted data access parameters accessible to the data consumer device.

15. The computer-implemented method of claim 10, wherein the data access policy defines restrictions on access to the data access key based on one or more of the data consumer identifier and a time at which the second request is received.

16. A non-transitory computer-readable storage medium comprising instructions which, when executed by a computer, cause the computer to carry out a method for secure information sharing comprising:

receiving a first request from a data owner device to define a data access key, the first request comprising data access parameters and a data access policy;

creating a data owner account for a data owner associated with the data owner device, the data owner account comprising a data owner public identifier to publicly identify the data owner and a data owner private identifier, the data owner private identifier not being publicly known;

encrypting the data access parameters to generate the data access key based on the data access parameters, wherein the data access parameters enable querying of a system of record to extract data records;

defining a data access control configuration based on the data access policy, the data access control configuration encoding data access rights of one or more data consumers;

transmitting to a distributed ledger network a request to store the data access key and the data access control configuration on the distributed ledger network;

receiving a second request to access the data records from a data consumer device, the second request comprising a data consumer identifier;

creating a data consumer account for a data consumer associated with the data consumer device, the data consumer account comprising a data consumer public identifier to publicly identify the data consumer and a data consumer private identifier, the data consumer private identifier not being publicly known;

responsive to the second request, generating and transmitting a third request to access the data records to the distributed ledger network, the third request comprising the data consumer identifier;

when the third request to access data records is determined to be valid, based on the data access control configuration, receiving the data access key from the distributed ledger network and making the received data access key accessible to the data consumer device.

* * * * *